(12) United States Patent
Collins et al.

(10) Patent No.: US 9,849,039 B2
(45) Date of Patent: Dec. 26, 2017

(54) THERAPEUTIC MEDICAL COMPRESSION GARMENT AND METHOD

(71) Applicant: BSN medical, Inc., Charlotte, NC (US)

(72) Inventors: Larry Wayne Collins, Connelly Springs, NC (US); Phillip Todd Clark, Granite Falls, NC (US); Joachim Dietmar Adof Bauer, Hamburg (DE)

(73) Assignee: BSN medical, Inc., Charlotte, NC (US)

( * ) Notice: Subject to any disclaimer, the term of this patent is extended or adjusted under 35 U.S.C. 154(b) by 607 days.

(21) Appl. No.: 14/451,486

(22) Filed: Aug. 5, 2014

(65) Prior Publication Data

US 2016/0038346 A1 Feb. 11, 2016

(51) Int. Cl.
| | |
|---|---|
| A61F 13/00 | (2006.01) |
| A61F 13/08 | (2006.01) |
| D04B 1/26 | (2006.01) |
| D04B 1/10 | (2006.01) |

(52) U.S. Cl.
CPC ........ *A61F 13/08* (2013.01); *A61F 13/00038* (2013.01); *A61F 13/00987* (2013.01); *D04B 1/106* (2013.01); *D04B 1/265* (2013.01); *A61F 2013/0028* (2013.01); *A61F 2013/00093* (2013.01); *A61F 2013/00119* (2013.01); *A61F 2013/00238* (2013.01)

(58) Field of Classification Search
CPC ............. A61H 1/008; A61F 13/000229; A61F 13/00036; A61F 13/00987; A61F 2013/00093; A61F 2013/00119
USPC .......................................... 602/60–62; 2/239
See application file for complete search history.

(56) References Cited

U.S. PATENT DOCUMENTS

| | | | | |
|---|---|---|---|---|
| 1,803,138 | A * | 4/1931 | Scott ...................... | D04B 1/106 66/188 |
| 2,154,124 | A * | 4/1939 | Cohn ..................... | D04B 1/106 66/173 |
| 3,122,906 | A * | 3/1964 | Crawford ............... | A41B 11/12 2/240 |
| 3,729,956 | A | 5/1973 | Nebel et al. | |
| 3,983,870 | A * | 10/1976 | Herbert .................. | A41B 11/12 2/240 |
| 4,149,274 | A * | 4/1979 | Garrou ................. | A41B 11/008 2/239 |
| 2003/0213269 | A1* | 11/2003 | Peeler ..................... | A61F 13/08 66/171 |

(Continued)

FOREIGN PATENT DOCUMENTS

| | | |
|---|---|---|
| EP | 1 079 017 A2 | 2/2001 |
| WO | 2011 116952 A1 | 9/2011 |
| WO | 2014 098928 A1 | 6/2014 |

OTHER PUBLICATIONS

International Search Report carried out by the European Patent Office for PCT/US2015/042569 dated Sep. 30, 2015.

*Primary Examiner* — Kim M Lewis
(74) *Attorney, Agent, or Firm* — Shumaker, Loop & Kendrick, LLP

(57) ABSTRACT

A therapeutic medical garment including a knitted welt proximate one end thereof with a surface adapted for residing against the wearer's skin. The garment includes a ground yarn and a plurality of raised, skin-engaging stabilizer elements, such as elongate bars extending in spaced-apart relation around an inner surface of the welt and along a longitudinal axis of the garment to reduce a tendency of the welt to roll over on itself.

13 Claims, 6 Drawing Sheets

(56) References Cited

U.S. PATENT DOCUMENTS

2010/0081984 A1* 4/2010 Coffinardi ............ A41B 11/126
      602/63
2010/0100024 A1* 4/2010 Reid, Jr. ................ A61F 13/08
      602/63

* cited by examiner

THERAPEUTIC MEDICAL COMPRESSION GARMENT AND METHOD

TECHNICAL FIELD AND BACKGROUND OF THE INVENTION

The present invention relates to a therapeutic medical compression garment. More particularly, the present invention relates to a therapeutic tubular compression hosiery garment having a welt formed at the top with structural features on the inner surface of the welt to contact the skin of the wearer. These structures reduce the tendency of the welt to roll down onto itself, and increase the resistance of the garment from slipping down the limb that is characteristic of prior art hosiery products. For purposes of illustration the invention disclosed in this application refers to garments used on the leg or parts of the length of the leg. The term "garment" is used in this application to mean garments such as body stockings, leg stockings, hose, panty-type hose, socks, arm sleeves and similar tubular structures used on the trunk, arms and legs. A method of constructing compression garments is also disclosed and claimed.

Therapeutic medical compression garments are used to assist in the management of various venous and lymphatic disorders, particularly in the lower extremities of the body. The purpose of the garment is to minimize or eliminate the effects of elevated venous pressures caused by gravity or disease processes by reducing the tendency of blood to pool in the lower extremities. This type of garment may also be applied to inactive or bedridden individuals to reduce the occurrence of clot formation in the lower extremities that can travel to the heart or lungs where a thromboembolism may develop. This type of garment functions by maintaining blood flow and typically has a graduated pressure profile to effect a predetermined compression of the leg sufficient to force blood upwardly out of the extremities and into circulation throughout the body. External circumferential counter pressure maintains the venous and lymphatic pressures at more normal level in the extremity, thus assisting the movement of venous blood and lymph from the extremity. Another important effect of compression is the reduction of venous volume that leads to an increase of venous flow velocity. Edema reduction and prevention is the goal in patients with chronic venous insufficiency, lymphedema, and other edema causing conditions. Subcutaneous pressures increase with elastic compression. This rise in subcutaneous tissue pressure acts to counter transcapillary forces, which favor leakage of fluid out of the capillary.

In order to ensure that the effect of an outside pressure or compression is constantly achieved to the correct extent and at the correct place on the body, it is necessary that the garment be kept in a therapeutically-correct position on the limb. For this purpose, it is known to include so called "anti-slip" structures into the garment. These structures are formed in such a manner that the garment is prevented from sliding along the limb due to the frictional properties of the yarns forming the knit structure and/or due to the elastic properties of the knit structure as a whole.

In addition, because medical efficacy often requires that compression garments be worn for a long period of time, it is desirable to control how much pressure is applied to the limb by the anti-slip structure in order to provide a comfortable fit for the wearer. An uncomfortable or even painful fit may induce the wearer to remove it, reducing or eliminating the desired therapeutic effect.

There are a variety of therapeutic medical compression garments that are known in the art. However, known therapeutic garments have a tendency to slip down the leg of the wearer, thereby detracting from the benefits of the garment. This slippage is often accompanied or caused by the top of the garment rolling down over itself to form a ring of fabric material at the top of the garment.

An example of a therapeutic garment is described in U.S. Pat. No. 3,975,929 to Fregeolle which describes a thigh length anti-embolism garment made with alternating courses of covered spandex yarn knitted on a circular hosiery knitting machine. The garment described in Fregeolle shows a turned welt around a portion of the top of the garment and a narrow elastic band stitched to the upper portion of the garment. The inner face of the elastic band is provided with beads or rows of frictional gripping material that aid in supporting the upper end of the garment on the leg of the wearer by frictionally engaging the leg.

Another example of a therapeutic garment is described in U.S. Pat. No. 3,874,001 to Patience, et al., which discloses a full length garment having a foot and leg portion knitted of elastic. A narrow band of non-slip elastomeric webbing material is sewn onto the upper end of the leg portion by over-stitching. The particular stitching used is said to provide for adequate movement of the knitting loops relative to each other to ensure the deformation of the garment as it is worn.

U.S. Pat. No. 3,983,870 to Herbert, et al. discloses a slip-resistant medical garment that addresses the "slip" problem by coating 20 to 30 percent of the inner surface of the knitted thread with a non-adhesive, non-continuous, relatively soft elastomeric polymeric material with a high coefficient of friction to provide a non-occlusive slip resistant-surface asserted to be capable of maintaining the support in place on the limb of the body.

Yet another type of anti-embolism garment is disclosed in U.S. Pat. No. 3,728,875 to Hartigan, et al. This garment is knitted on a circular hosiery knitting machine and the upper portion is slit downwardly in a walewise direction. A wedge-shaped insert of soft elastic fabric is sewn into the slit to increase the circumference of the upper end of the garment. In garments of this type the sewing of the wedge increases the cost of production. The insert is formed of a different compressive fabric than the remaining portion of the upper end of the garment so that the portion of the leg covered by the insert does not receive the same compressive force as applied to the remaining portion of the leg of the wearer. The garment also has a partial elastic retention band made with a corrugated anti-slip inner surface of urethane elastomer sewn to the upper narrow welt of the garment and projecting above the garment welt so that its top forms a continuous line with the top of the insert.

A more recent compression garment is disclosed in U.S. Pat. No. 6,871,516 to Peeler, et al. The garment disclosed in Peeler is a therapeutic medical compression garment with a knitted anti-slip portion located in the upper area of the garment. The garment functions by placing high friction yarns that comprise part of the welt directly next to the wearer's skin in the area of the welt. The high-friction characteristics result from the inherent qualities of the yarn and the texture formed on the inner side of the welt during the knitting process. However, anti-slip effects achieved solely or principally from the inherent characteristics of the yarns may mimic the effects of other types of high-friction creating materials, such as exposed rubber bands and silicone strips or dots which may pull on body hair as the garment creeps down the leg, causing discomfort.

In addition, as noted above, welts of known compression garments have a tendency to roll downwardly over themselves, which may not only initiate further creeping of the garment down the leg, but can also increase compressive force at the rollover site on the leg, restricting blood flow past the rollover site, and thereby counteracting the otherwise beneficial effects of the progressive compression that is intended to force blood upwardly out of the extremities.

Thus, while improvements have been made to the anti-slip properties of anti-embolism garments there remains a need for an effective, inexpensive therapeutic medical compression garment that will resist slipping down the leg of the wearer and that avoids rollover of the welt and the potentially detrimental effects that can result.

SUMMARY OF THE INVENTION

Therefore, it is an object of the present invention to provide a therapeutic garment having effective anti-slip properties.

It is an object of the present invention to provide a therapeutic garment that has a welt with effective means for avoiding rolling over of the welt on itself during wear.

It is a further object of the invention to provide a therapeutic medical compression garment which does not require sewing a separate elastomeric element to the upper end of the garment.

It is a further object of the present invention to provide an anti-slip garment without structures that may cause high pressure at sites on the limb, such as with bulky seams, band overlaps/joints, or strips or dots of silicone.

The body of the garment is preferably a circular knit garment produced in any manner known to those skilled in the art, such as jersey stitches.

According to another embodiment of the invention, the ground yarns of the welt comprise a jersey knit structure.

According to another embodiment of the invention, a circular-knitted garment is provided for being worn on the leg, wherein stabilizer elements include a knitted structure extending substantially longitudinally along at least part of the length of the welt on an inner surface. A first feed comprises a jersey knit on all needles with a plurality of spaced-apart stabilizer bar yarns patterned into the welt around a circumference of the welt. A second feed comprises a jersey knit on all needles with a plurality of spaced-apart float yarns patterned into the welt to provide additional bulk to the stabilizer elements. A third feed comprises a jersey knit on all needles with a plurality of spaced-apart stabilizer bar yarns patterned into the welt around the circumference of the welt. A fourth feed comprises an inlaid 1×1 rib knitted at tuck height.

According to another embodiment of the invention, the welt is a turned welt having an inner surface and a separated outer surface joined at a top edge of the welt, wherein the welt comprises between 80 and 100 knitting revolutions. The stabilizer elements formed in the welt prevent the top of the welt from deflecting outwardly away from the longitudinal axis. Thus, the stabilizer elements counteract forces generated by the tension in the knit structure when being worn that would otherwise deflect the welt outwardly and cause the welt to roll over and down on itself. The welt is therefore maintained in a position where even the free or distal end of the welt resides in a flat, unrolled condition on the wearer's limb.

According to another embodiment of the invention, the annular welt includes an inwardly facing layer and an outwardly facing layer with stabilizer elements configured so that in the use condition the modulus of elasticity parallel to the longitudinal axis of the inwardly facing layer is increased in comparison to the modulus of elasticity parallel to the longitudinal axis of the inwardly facing layer without the stabilizer elements. The layers define respective surfaces.

The welt of the garment includes an inwardly facing layer and an outwardly facing layer. In particular, the outwardly and inwardly facing layers may be formed as separate layers running in parallel, with the layers connected to each other along a first annular line forming one end of the garment and another annular line spaced from the first line. Alternatively, the layers may not be separated but connected along lines at the respective ends only.

According to an embodiment of the invention, in the use condition the elastic modulus of the inner layer is increased compared to the locations on the garment where there are no stabilizer elements. In this regard, the term "use condition" means that the garment is expanded to such a state that it has the dimensions which it has when being worn on a wearer's limb. The stabilizer elements are designed and distributed such that in the use condition the modulus of elasticity parallel to the longitudinal direction is increased. Thus, the resistance of the inwardly facing layer against a lengthening stress parallel to the longitudinal axis is increased. Whenever the welt begins to roll back on itself, the inwardly facing layer will lengthen. As the resistance against a lengthening is increased, the welt becomes more stable and is effectively prevented from starting to deflect outwardly and to roll over itself.

According to another embodiment of the invention, in order to achieve the effect of an increase of the elastic modulus parallel to the longitudinal axis, in the use condition of the garment the stabilizer elements are prestressed such that they apply a force that tends to contract the inwardly facing layer parallel to the longitudinal axis. The term "prestressed" as used above means that at least when the garment is in the above-referenced use condition, the stabilizer elements are expanded parallel to the longitudinal axis compared to a relaxed state so that the stabilizer elements exert a force to the inwardly facing layer that tends to contract this layer. At the same time such a force does not act on the outwardly facing layer so that there is a tendency of the entire end to deflect inwardly.

According to another preferred embodiment, the stabilizer elements are formed on a surface of the welt that faces inwardly towards the longitudinal axis. In the use condition the stabilizer elements are subject to tensile stress parallel to the longitudinal axis. The tensile stress generated in the stabilizer elements when the garment is in the use condition causes these elements to tend to contract. This tendency is transferred to the inwardly facing surface of the welt because the stabilizer elements and the welt are integral with each other. This contracting force results in the inwardly facing side of the welt having an increased resistance against a lengthening which would otherwise occur when the end portion deflects outwardly and starts to roll over itself.

According to another preferred embodiment of the invention, the welt includes first and second annular sections which are connected along a circular connection line forming the end of the garment. The first section faces inwardly towards the longitudinal axis and the second section faces outwardly away from the longitudinal axis. Stabilizer elements are formed on the first section and/or stabilizer elements are formed on the second section. The stabilizer elements on the first section are subject to tensile stress parallel to the longitudinal axis and the stabilizer elements on the second section are subject to compressive stress parallel to the longitudinal axis when the garment is in the use condition. The welt is formed having an inwardly facing section and an outwardly facing section which are connected along a circular connection line forming one end of the garment. In addition, the inwardly facing section and the outwardly facing section are connected with each other along a second connection line spaced from the line forming the end of the garment. Between these lines the sections are separated from each other so that they may slide on each other.

If stabilizer elements are provided on the inwardly facing section, in the use condition the stabilizer elements are subject to tensile stress so that they tend to contract which leads to an increased resistance against lengthening. As noted above, this prevents both sections from deflecting outwardly away from the longitudinal axis.

In addition to or as an alternative, the outwardly facing section can be provided with stabilizer elements which in the use condition are subject to compressive stress. This means that these stabilizer elements tend to expand in the direction parallel to the longitudinal axis of the garment. As the stabilizer elements and the outwardly facing section are connected with each other, in the use condition this section also tends to expand parallel to the longitudinal axis.

However, when the welt formed of the two sections would roll over itself the outwardly facing section would need to be contracted in the longitudinal direction. Thus, the arrangement of stabilizer elements on the outwardly facing section of the welt being subject to compressive stress also increases the resistance against an outward deflection of the sections.

Preferably, the stabilizer elements are arranged in spaced-apart relation on a surface of the welt. The stabilizer elements are elongate and extend in a lengthwise direction along longitudinal axis of the welt with a substantially smaller transverse width. In a further preferred embodiment, the longitudinal direction of the stabilizer elements is parallel to the longitudinal axis of the garment.

According to alternative embodiment, the stabilizer elements are diagonal to the longitudinal axis of the garment so that the stabilizer elements have both a parallel and circumferential directional component around at least a part of a circumference of the welt.

The stabilizer elements increase the resistance of the welt against lengthening in response to a longitudinal stress. In addition, because the raised stabilizer elements have enhanced stability in the direction along which they extend, this stability is transferred to the welt itself which prevents an outward rollover. Thus, without regard to whether the stabilizer elements are parallel to or diagonal to the longitudinal axis of the garment, the welt is less likely to roll down onto itself.

According to another embodiment of the invention, a therapeutic medical garment is provided comprising a knitted body and a knitted welt proximate one end of the body with a surface adapted for residing against the wearer's skin, including a ground yarn and a plurality of raised stabilizer elements extending in spaced-apart relation around the welt to reduce a tendency of the welt to roll on itself.

According to another embodiment of the invention, the stabilizer elements extend along a longitudinal axis of the garment on an inner surface of the welt.

According to another embodiment of the invention, the welt comprises a turned welt integrally-knitted with the knitted body, and has a separate outer surface and an inner surface joined at and defining one end of the garment.

According to another embodiment of the invention, the stabilizer elements comprise a covered elastomeric yarn.

According to another embodiment of the invention, an angle of extension of the stabilizer elements have a component extending along the longitudinal axis of the garment and a component extending radially around at least a portion of a circumference of the garment.

According to another embodiment of the invention, the stabilizer elements are integrally-knitted into the structure of the welt.

According to another embodiment of the invention, the stabilizer elements are separate elements applied and secured to an inner surface of the welt.

According to another embodiment of the invention, a therapeutic medical garment is provided, having a graduated pressure profile along its length, and comprising a knitted body, a welt having a separate outer surface and an inner surface joined at and defining an upper end of the garment, including a ground yarn and a plurality of stabilizer elements extending in spaced-apart relation around the welt and along a longitudinal axis of the garment to reduce a tendency for the welt to roll onto itself, and an anti-slip portion formed intermediate the body and the welt and having a textured inner surface adapted for residing in a non-slip condition against the wearer's skin to increase the anti-slip properties of the garment.

According to another embodiment of the invention, the knitted body, anti-slip portion and welt are integrally-formed.

According to another embodiment of the invention, the welt has at least four stabilizer elements.

According to another embodiment of the invention, the inner welt surface and the outer welt surface include ground yarns formed of covered elastomeric yarns.

According to another embodiment of the invention, the ground yarns of the welt comprise a jersey knit structure.

According to another embodiment of the invention, the garment comprises a circular-knitted stocking for being worn on the leg, and the welt comprises a plurality of knitting revolutions, wherein the stabilizer elements comprise a knitted structure extending substantially longitudinally along a length of the welt on an inner surface. The knitting revolutions include a first feed comprising a jersey knit on all needles with a plurality of spaced-apart stabilizer bar yarns patterned into the welt around a circumference of the welt, a second feed comprising a jersey knit on all needles with a plurality of spaced-apart float yarns patterned into the welt to provide additional bulk to the stabilizer elements, a third feed comprising a jersey knit on all needles with a plurality of spaced-apart stabilizer bar yarns patterned into the welt around the circumference of the welt, and a fourth feed comprising an inlaid 1×1 rib knitted at tuck height.

According to another embodiment of the invention, the outer surface of the welt includes in a plurality of knitting revolutions forming the circular-knitted welt, which have a first feed comprising a jersey knit on all needles around a circumference of the welt, a second feed comprising a jersey knit on all needles around the circumference of the welt, a third feed comprising a jersey knit on all needles around the circumference of the welt, and a fourth feed comprising an inlaid 1×1 rib at tuck height around the circumference of the welt.

According to another embodiment of the invention, a therapeutic medical garment having a graduated pressure profile along its length is provided, and comprises a knitted welt proximate one end thereof with a surface adapted for residing against the wearer's skin constructed of a ground yarn and a plurality of raised, skin-engaging stabilizer elements extending in spaced-apart relation around an inner surface of the welt to reduce a tendency of the welt to roll on itself. The garment comprises a circular-knitted stocking for being worn on a leg, the stabilizer elements comprise a knitted structure extending substantially longitudinally along a length of the welt on an inner surface and include in a plurality of knitting revolutions forming the circular-knitted welt a first feed comprising a jersey knit on all needles with a plurality of spaced-apart stabilizer bar yarns patterned into the welt around a circumference of the welt, a second feed comprising a jersey knit on all needles with a plurality of spaced-apart float yarns patterned into the welt to provide additional bulk to the stabilizer elements, a third feed comprising a jersey knit on all needles with a plurality of spaced-apart stabilizer bar yarns patterned into the welt around the circumference of the welt, and a fourth feed comprising an inlaid 1×1 rib knitted at tuck height.

According to another embodiment of the invention, a method of constructing a therapeutic medical garment is provided and includes the steps of knitting a garment having a welt proximate one end with a surface adapted for residing against the wearer's skin, and positioning a plurality of raised, skin-engaging stabilizer elements on an inner surface of the welt in spaced-apart relation around the inner surface of the welt to reduce a tendency of the welt to roll on itself.

According to another embodiment of the invention, the step of positioning a plurality of raised, skin-engaging stabilizer elements on an inner surface of the welt includes the step of extending the stabilizer elements along a longitudinal axis of the garment.

According to another embodiment of the invention, the step of knitting a garment having a welt includes the step of integrally-knitting a turned welt having a separate outer surface and an inner surface joined at and defining one end of the garment.

According to another embodiment of the invention, the method includes the step of forming the stabilizer elements with a covered elastomeric yarn.

According to another embodiment of the invention, the method includes the step of forming the stabilizer elements on the welt to extend diagonally along the length of the garment.

According to another embodiment of the invention, the step of positioning a plurality of raised, skin-engaging stabilizer elements on an inner surface of the welt includes the step of integrally-knitting the stabilizer elements into the structure of the garment and providing a graduated pressure profile along its length.

According to another embodiment of the invention, the step of positioning a plurality of raised, skin-engaging stabilizer elements on an inner surface of the welt includes the steps of forming the stabilizer elements as separate elements and applying and securing the stabilizer elements to an inner surface of the welt.

According to another embodiment of the invention, the step of positioning a plurality of raised, skin-engaging stabilizer elements on an inner surface of the welt includes the steps of forming the stabilizer elements as separate elements and applying and securing the stabilizer elements to an inner surface of the welt according to a securing method selected from the group consisting of gluing, welding, fusing, melting and sewing the stabilizer elements onto the knit structure of the welt.

According to another embodiment of the invention, a therapeutic medical garment having a graduated pressure profile along its length is provided, and comprising a knitted garment having a knitted welt proximate one end of the garment with an inwardly facing layer having a surface adapted for residing against a wearer's skin. The welt includes a ground yarn and a plurality of raised, skin-engaging stabilizer elements positioned on and extending in spaced-apart relation around either the inwardly facing or outwardly facing surface of the welt. Either the outwardly facing layer or the inwardly facing layer is configured so that in a use condition on a limb of a wearer a modulus of elasticity parallel to a longitudinal axis of one of the layers is greater than a modulus of elasticity parallel to the longitudinal axis of the other layer. A resistance of the one of the layers against a lengthening stress parallel to the longitudinal axis is increased such that if the welt begins to roll back on itself, the layer will lengthen, and as the resistance against a lengthening increases, the welt becomes more stable and is prevented from deflecting outwardly and rolling over itself.

According to another embodiment of the invention, the inwardly facing layer and the outwardly facing layer of the welt define a first annular connection at a top end of the garment, a second annular connection on the garment at a longitudinally spaced-apart location from the first annular connection. A length of the inwardly facing layer and the outwardly facing layer between the first and second annular connections are separate from each other and define the longitudinal extent of the welt.

According to another embodiment of the invention, in a use condition on a limb of a wearer the stabilizer elements are prestressed such that they apply a force that tends to contract the inwardly facing layer parallel to the longitudinal compared to a relaxed state whereby the stabilizer elements exert a force to the inwardly facing layer that tends to contract the inwardly facing layer but does not exert a force on the outwardly facing layer, thereby creating a tendency of the welt to deflect inwardly in opposition to a tendency of the welt to roll outwardly over itself.

According to another embodiment of the invention, the stabilizer elements are integrally formed with the inwardly facing layer of the welt.

According to another embodiment of the invention, the garment comprises a stocking.

BRIEF DESCRIPTION OF THE DRAWING FIGURES

The present invention is best understood when the following detailed description of the invention is read with reference to the accompanying drawings, in which.

Figure 5:
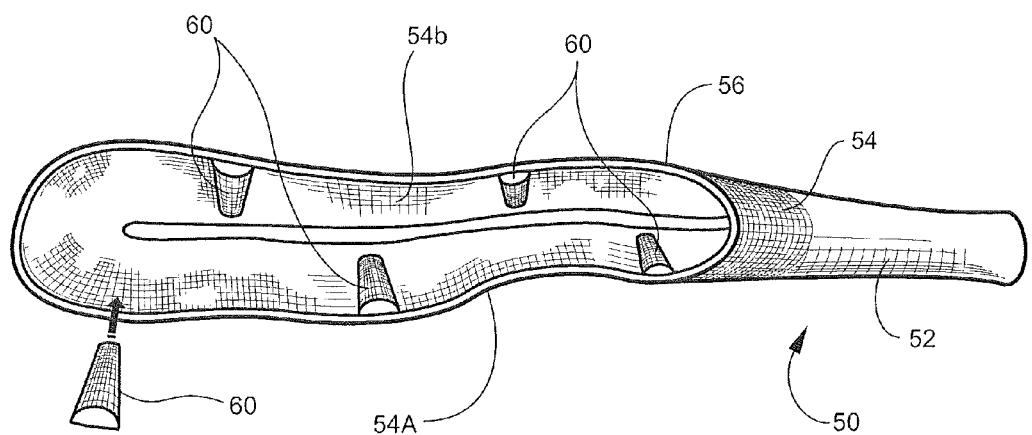
Figure 6:
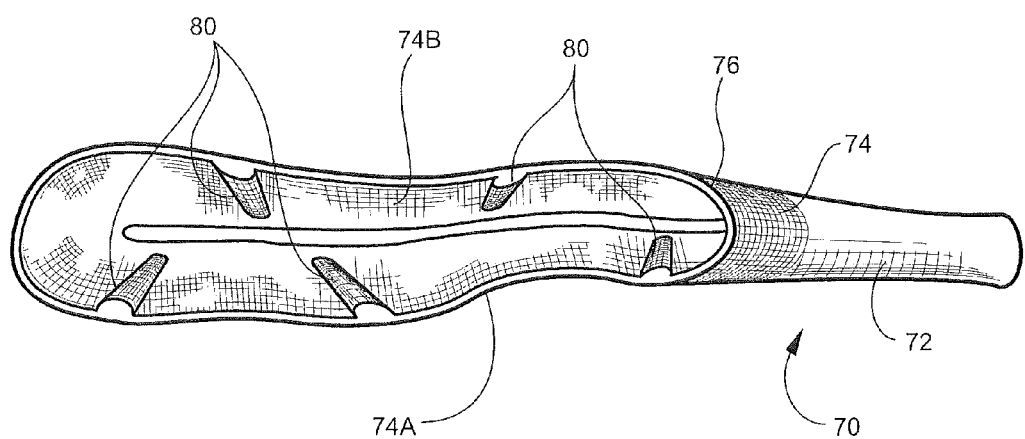

FIG. 5 is a top view of an alternative embodiment of a hosiery product according to the present invention, showing stabilizer elements formed as separate elements and attached to the welt as, for example, by an adhesive or by sewing; and FIG. 6 is a top view of yet another alternative embodiment of a hosiery product according to the present invention, showing stabilizer elements that have an angle of extension with a component extending longitudinally along the length of the garment and a component extending radially around at least a portion of a circumference of the garment.

DETAILED DESCRIPTION OF THE PREFERRED EMBODIMENT

Referring now specifically to the drawings, a therapeutic medical compression garment in the form of a compression stocking is shown broadly at reference numeral 10. While, as noted above, the invention is described in this application for purposes of illustration as a compression stocking, the invention also includes any garments, such as stockings, sleeves, socks, hose, panty-type hose and the like that when worn assist in the management of venous or lymphatic disorders and/or thrombosis in the limb of a wearer.

Figure 1:
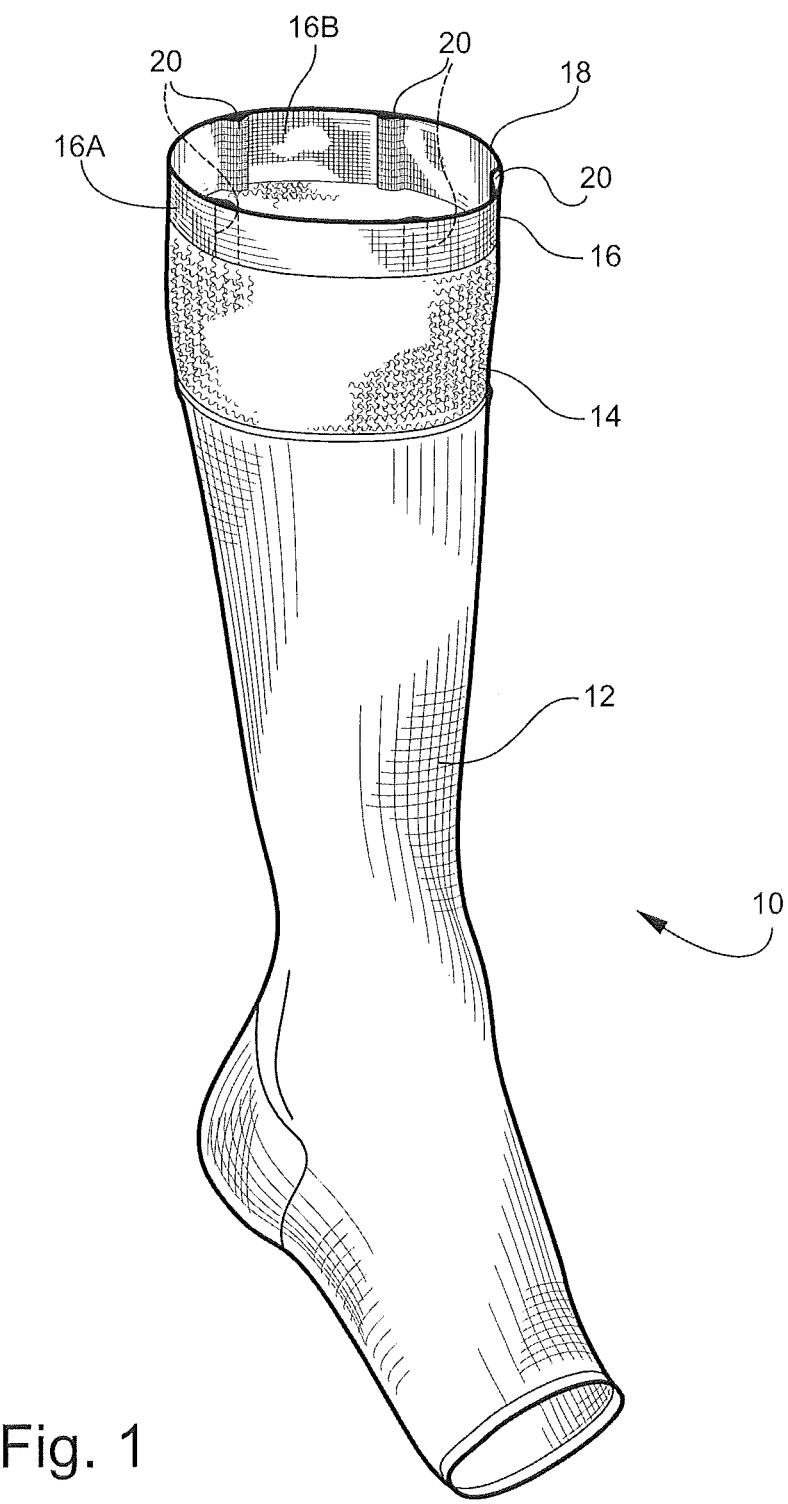
FIG. 1 is a perspective view of a medical garment in the form of a compression hosiery product according to one embodiment of the invention.

Stocking 10 according to the particular embodiment of FIG. 1 has a body portion 12, an anti-slip portion 14 formed as part of the stocking's body fabric located toward the upper end of the stocking 10, and a welt 16 at the top end of the stocking 10.

The body 12 of the stocking 10 is preferably circular knit in a manner known to those skilled in the art, for example, utilizing jersey stitches. The stretchable textured yarn is knit in jersey courses. The stocking 10 may be knitted on any conventional knitting machine, such as a Santoni Pendolina medical knitting machine or a Lonati La-ME medical knitting machine.

The anti-slip portion 14 of the stocking 10 is optionally knitted into the stocking 10 to provide a raised surface texture, and a preferred embodiment of the yarn construction and knit construction for two frequently used knitting machines is set out below:

Yarn Construction: "Santoni Pendolina Medical Knitting Machine"

1st Feed: 1/70/34 Stretch Nylon (S Twist)
2nd Feed: Roica C-701-420 denier Spandex
3rd Feed: 1/100/34 Stretch Nylon (Z Twist)
4th Feed: Roica C-701-117 denier Spandex Yarn Construction: "Lonati LA-ME Medical Knitting Machine"

1st Feed: Roica C-701-420 denier Spandex
2nd Feed: 1/100/34 Stretch Nylon (Z Twist)
3rd Feed: Roica C-701-117 denier Spandex
4th Feed: 1/70/34 Stretch Nylon (S Twist)

Knit Construction: "Santoni Pendolina Medical Knitting Machine"

1st Feed: Jersey knit on all needles
2nd Feed: 2×2 Alternating mesh pattern (for inlay purposes)
3rd Feed: Jersey knit on all needles
4th Feed: 2×2 Alternating mesh pattern (for inlay purposes)

Knit Construction: "Lonati LA-ME Medical Knitting Machine"

1st Feed: 2×2 Alternating mesh pattern (for inlay purposes)
2nd Feed: Jersey knit on all needles
3rd Feed: 2×2 Alternating mesh pattern (for inlay purposes)
4th Feed: Jersey knit on all needles The welt 16 includes a separate outer surface 16A and an inner surface 16B joined at and defining an upper end 18 of the stocking 10, including a ground yarn and a plurality of integrally-knitted, raised, skin-engaging stabilizer elements 20 preferably formed of an elastomeric yarn preferably covered with a multi-filament synthetic yarn. The stabilizer elements 20, which may in some embodiments resemble elongate "bars", extend in spaced-apart relation around the welt 16 and along a longitudinal axis of the stocking 10 to reduce a tendency for the welt 16 to roll outwardly away from the limb and onto itself. In this and in the embodiments described below, the term "stabilizer elements" is intended to convey that there are structures, either integrally-formed or separately applied, that extend away from the surrounding stocking fabric to engage the body part to which it is applied. The body part and the structure of the stabilizing elements together reduce the a tendency for the welt 16 to roll outwardly away from the limb and onto itself.

Note that because the stocking 10 has a tubular shape, it defines an axis along which it extends. Therefore, the term "longitudinal axis" does not mean that the longitudinal axis is necessarily straight or linear but may also be curved in a manner that facilitates conformation to the limb on which it is worn.

The stabilizer elements 20 shown in the application have an elongate orientation that extend along the longitudinal axis of the stocking 10. However, stabilizer elements according to other constructions may have different orientations, including forming shapes such as chevrons, X-shaped configurations having both longitudinal and radial angular components, as well as singularly-extending elements, either elongate or non-elongate, with both longitudinal and radial angular components that define a generally diagonal direction.

Inner Welt-Yarn Construction: "Santoni Pendolina Medical Knitting Machine"

1st Feed: 1/70/34 Stretch Nylon (S Twist)
(Stabilizer Elements) 140 denier Spandex double covered with 1/15/5 nylon
2nd Feed: 20 denier spandex double covered with 1/40/34 nylon
3rd Feed: 20 denier spandex double covered with 1/40/34 nylon
(Stabilizer Elements) 140 denier Spandex double covered with 1/15/5 nylon
4th Feed: Roica C-701-117 denier Spandex Inner Welt-Yarn Construction: "Lonati LA-ME Medical Knitting Machine"

1st Feed: 20 denier spandex double covered with 1/40/34 nylon
(Stabilize Elements) 140 denier Spandex double covered with 1/15/5 nylon
2nd Feed: 20 denier spandex double covered with 1/40/34 nylon
3rd Feed: Roica C-701-117 denier Spandex
4th Feed: 1/70/34 Stretch Nylon (S Twist)
(Stabilizer Elements) 140 denier Spandex double covered with 1/15/5 nylon Outer Welt-Yarn Construction: "Santoni Pendolina Medical Knitting Machine"

1st Feed: 1/70/34 Stretch Nylon (S Twist)
2nd Feed: 20 denier spandex double covered with 1/40/34 nylon
3rd Feed: 20 denier spandex double covered with 1/40/34 nylon
4th Feed: Roica C-701-117 denier Spandex Outer Welt-Yarn Construction: "Lonati LA-ME Medical Knitting Machine"

1st Feed: 20 denier spandex double covered with 1/40/34 nylon
2nd Feed: 20 denier spandex double covered with 1/40/34 nylon
3rd Feed: Roica C-701-117 denier Spandex
4th Feed: 1/70/34 Stretch Nylon (S Twist)

Inner Welt-Knit Construction: "Santoni Pendolina Medical Knitting Machine"

1st Feed: Jersey knit on all needles with five (5) "6 needle wide Stabilizer Elements patterns" being patterned into the garment.
2nd Feed: Jersey knit on all needles except for five (5) "6 needle wide FLOAT patterns" being patterned into the garment to add additional bulk to the "Stabilizer Elements".
3rd Feed: Jersey knit on all needles with five (5) "6 needle wide Stabilizer Elements pattern" being patterned into the garment
4th Feed: 1×1 rib at tuck height (for inlay purposes)

Inner Welt-Knit Construction: "Lonati LA-ME Medical Knitting Machine"

1st Feed: Jersey knit on all needles except for five (5) "6 needle wide FLOAT patterns" being patterned into the garment to add additional bulk to the "Stabilizer Elements".
2nd Feed: Jersey knit on all needles with five (5) "6 needle wide Stabilizer Elements patterns" being patterned into the garment.
3rd Feed: 1×1 rib at tuck height (for inlay purposes)
4th Feed: Jersey knit on all needles with five (5) "6 needle wide Stabilizer Elements patterns" being patterned into the garment.

Outer Welt-Knit Construction: "Santoni Pendolina Medical Knitting Machine"

1st Feed: Jersey knit on all needles
2nd Feed: Jersey knit on all needles
3rd Feed: Jersey knit on all needles
4th Feed: 1×1 rib at tuck height (for inlay purposes)

Outer Welt-Knit Construction: "Lonati LA-ME Medical Knitting Machine"

1st Feed: Jersey knit on all needles
2nd Feed: Jersey knit on all needles
3rd Feed: 1×1 rib at tuck height (for inlay purposes)
4th Feed: Jersey knit on all needles By way of example, the elastomeric yarns knit at pattern height on feeds 1 and 3. These elastomeric yarns are introduced separately during knitting over 6 needles and then cut. When relaxed, these yarns recoil into a relaxed state causing the stitches formed by the ground yarns to bunch together and form the "stabilizing elements", which have the general shape of an elongate "bar."

Figure 2:
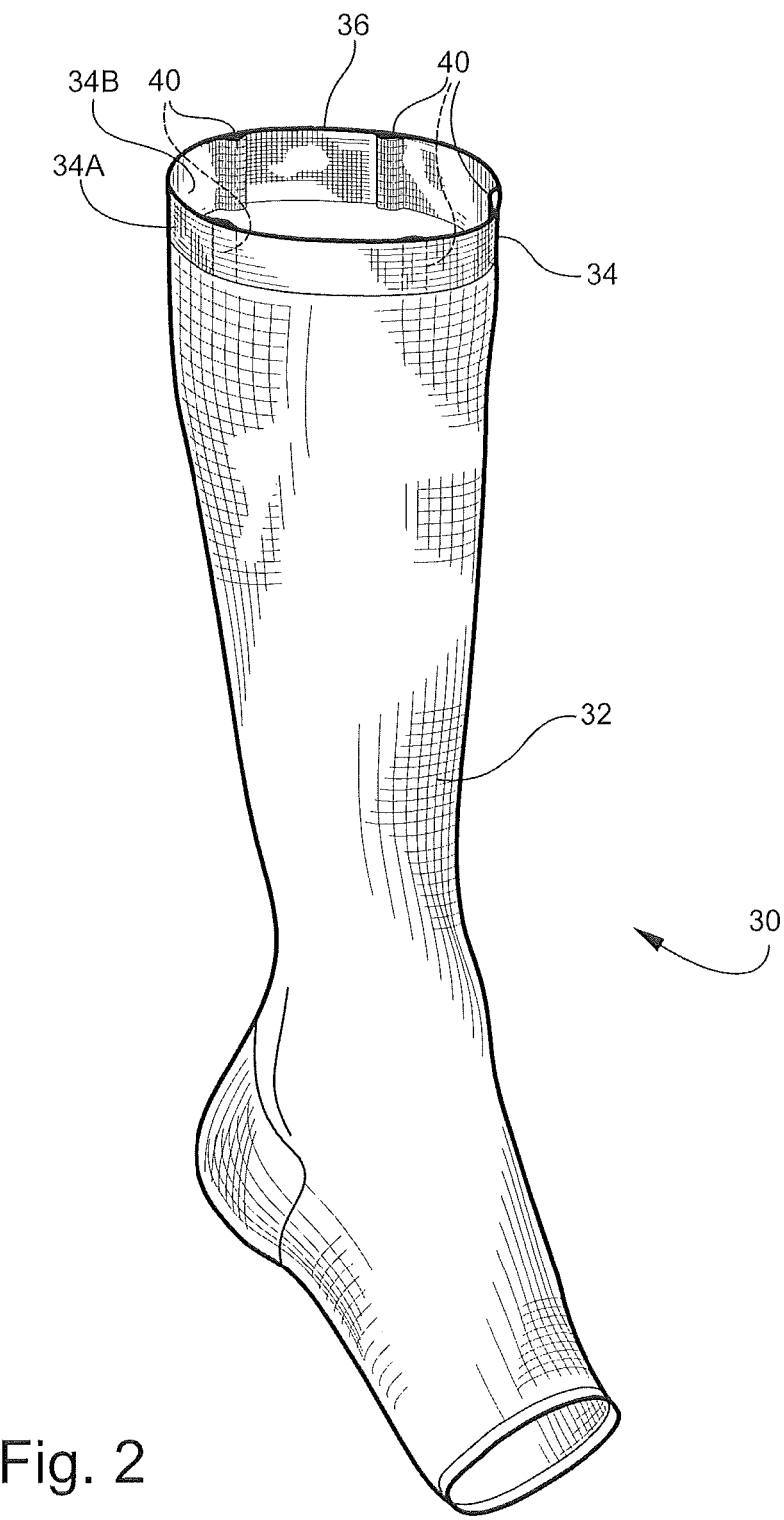
FIG. 2 is a perspective view of a medical garment in the form of a compression hosiery product according to another embodiment of the invention.

Referring now to FIG. 2, another garment according to the invention is shown as a stocking 30, and includes a body portion 32, and a welt 34 at the top end of the stocking 30. The knit and yarn constructions set out above may be utilized with the stocking 30, as well.

The welt 34 includes a separate outer surface 34A and an inner surface 34B joined at and defining an upper end 36 of the stocking 30. The welt 34 includes a ground yarn and a plurality of integrally-knitted, raised, skin-engaging stabilizer elements 40 preferably formed of an elastomeric yarn covered with a multi-filament synthetic yarn extending in spaced-apart relation around the welt 34 and along a longitudinal axis of the garment 30 to reduce a tendency for the welt 34 to roll outwardly and onto itself. The yarn construction and the knitting construction for the welt 34 is preferably the same as for the welt 16, set out above.

Figure 3:
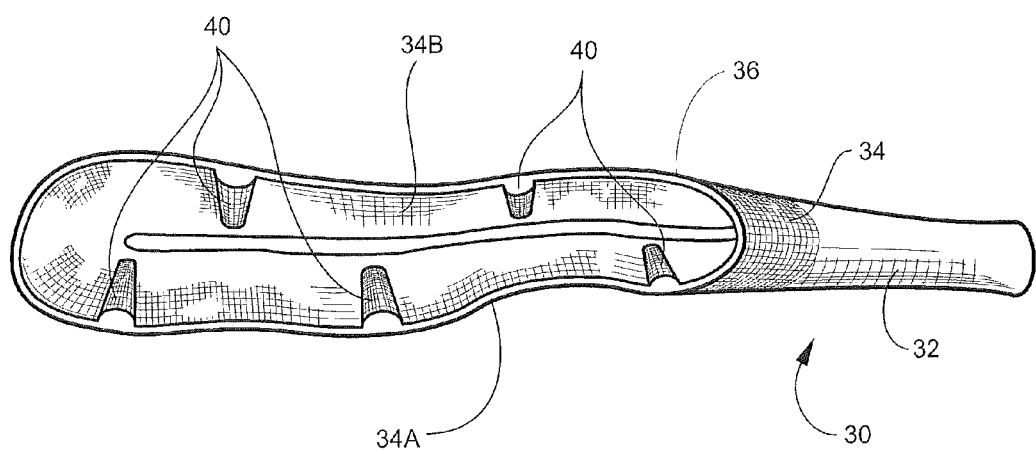
FIG. 3 is a top view of the hosiery product shown in FIG. 2 showing the stabilizer elements according to one embodiment of the invention extending along a longitudinal dimension of the hosiery product.

The stabilizer elements 20 and 40 of the stockings 10 and 30 have a distinct thickness that causes them to extend inwardly towards the limb above the level of the adjacent ground yarns to engage the skin of the wearer, but which are nevertheless soft enough not to bite into the skin. The welt 34 and stabilizer elements 40 are shown by way of example in FIG. 3.

Figure 4:
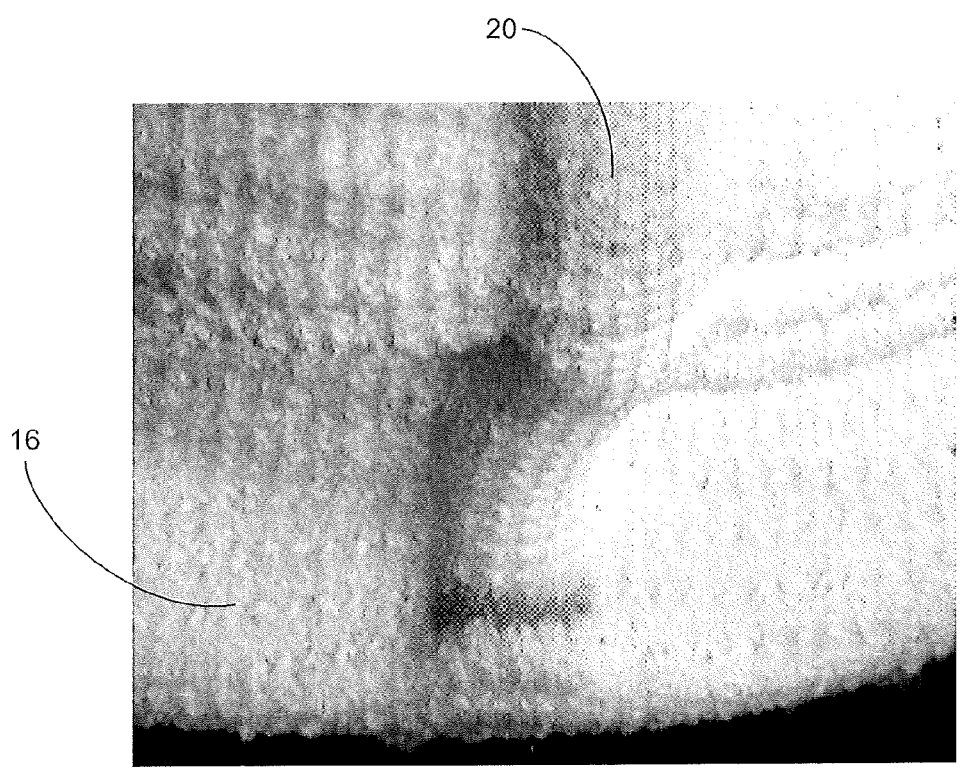
FIG. 4 is a photomicrograph of a section of the inner welt of a hosiery garment according to one embodiment of the invention, and showing one of the stabilizer elements.

A microphotograph of the welt 16 showing a stabilizer bar 20 is shown in FIG. 4.

As is shown in FIG. 5, another garment according to the invention is shown as a stocking 50, and includes a body portion 52, and a welt 54 at the top end of the stocking 50. The knit and yarn constructions set out above may be utilized with the stocking 50, as well.

The welt 54 includes a separate outer surface 54A and an inner surface 54B joined at and defining an upper end 56 of the stocking 50. The welt 54 includes a ground yarn and a plurality of integrally-knitted, raised, skin-engaging stabilizer elements 60 preferably formed of an elastomeric yarn covered with a multi-filament synthetic yarn extending in spaced-apart relation around the welt 54 and along a longitudinal axis of the garment 50 to reduce a tendency for the welt 54 to roll outwardly and onto itself. The yarn construction and the knitting construction for the welt 54 is preferably the same as for the welt 16, set out above.

As shown in FIG. 5, the raised stabilizer elements 60 may be formed by other methods, for example, by utilizing a melt yarn in a separately-formed stabilizer bar 60 by fusing or welding the stabilizer bar 60 in the desired position on the inner surface of the welt 54, by applying the stabilizer elements 60 to the welt 54 as appliqués, by gluing the stabilizer elements 60 onto the welt 54, or by sewing the stabilizer elements 60 with stitches, such as straight, zig-zag or overedge seaming stitches, onto the welt 54.

Referring now to FIG. 6, a stocking 70 according to another embodiment of the invention and includes a body portion 72, and a welt 74 at the top end of the stocking 70. The knit and yarn constructions set out above may be utilized with the stocking 70, as well.

The welt 74 includes a separate outer surface 74A and an inner surface 74B joined at and defining an upper end 76 of the stocking 70. The welt 74 includes a ground yarn and a plurality of integrally-knitted, raised, skin-engaging stabilizer elements 80 preferably formed of an elastomeric yarn covered with a multi-filament synthetic yarn extending in spaced-apart relation around the welt 74 and along a longitudinal axis of the garment 70 to reduce a tendency for the welt 74 to roll outwardly and onto itself. The yarn construction and the knitting construction for the welt 54 is preferably the same as for the welt 16, set out above.

The stabilizer elements 70 have an angle of extension that has a component that is aligned with the longitudinal axis of the stocking 70 and a component that extends radially around at least a part of a circumference of the stocking 70 to form a diagonal array of stabilizer elements 70.

In the embodiments illustrated and described above, the garments are preferably constructed with a graduated pressure profile in order to effect a predetermined compression of the leg sufficient to force blood upwardly out of the extremities and into circulation throughout the body. External circumferential counter pressure maintains the venous and lymphatic pressures at a more normal level in the extremity, thus assisting the movement of venous blood and lymph from the extremity. This feature is known in the art, as exemplified in the prior art references described above. However, garments of the general type described in this application can be constructed according to embodiments of the invention without the graduated compression feature.

A therapeutic medical garment and a method of constructing a therapeutic medical garment according to the invention have been described with reference to specific embodiments and examples. Various details of the invention may be changed without departing from the scope of the invention. Furthermore, the foregoing description of the preferred embodiments of the invention and best mode for practicing the invention are provided for the purpose of illustration only and not for the purpose of limitation.

We claim:

1. A therapeutic medical garment having a graduated pressure profile along its length, and comprising:
   (a) a knitted body;
   (b) a welt having a separate outer surface and an inner surface joined at and defining an upper end of the garment, including a ground yarn and a plurality of stabilizer elements extending in spaced-apart relation around the welt and along a longitudinal axis of the garment to reduce a tendency for the welt to roll onto itself; and
   (c) an anti-slip portion formed intermediate the body and the welt and having a textured inner surface adapted for residing in a non-slip condition against a wearer's skin to increase anti-slip properties of the garment, wherein the garment comprises a circular-knitted stocking for being worn on a leg, and the welt comprises a plurality of knitting revolutions, wherein the stabilizer elements comprise a knitted structure extending substantially longitudinally along a length of the welt on an inner surface thereof, and formed from:
   (a) a first feed comprising a jersey knit on all needles with a plurality of spaced-apart stabilizer bar yarns patterned into the welt around a circumference of the welt;
   (b) a second feed comprising a jersey knit on all needles with a plurality of spaced-apart float yarns patterned into the welt to provide additional bulk to the stabilizer elements;
   (c) a third feed comprising a jersey knit on all needles with a plurality of spaced-apart stabilizer bar yarns patterned into the welt around the circumference of the welt; and
   (d) a fourth feed comprising an inlaid 1×1 rib knitted at tuck height.

2. The therapeutic garment according to claim 1, wherein the knitted body, anti-slip portion and welt are integrally-formed.

3. The therapeutic garment according to claim 1, wherein the welt has at least four stabilizer elements.

4. The therapeutic garment according to claim 1, wherein the inner welt surface and the outer welt surface include ground yarns formed of covered elastomeric yarns.

5. The therapeutic garment according to claim 1, wherein the ground yarns of the welt comprise a jersey knit structure.

6. A therapeutic medical garment according to claim 1, wherein the outer surface of the welt includes in a plurality of knitting revolutions forming the circular-knitted welt formed from:
   (a) a first feed comprising a jersey knit on all needles around a circumference of the welt;
   (b) a second feed comprising a jersey knit on all needles around the circumference of the welt;
   (c) a third feed comprising a jersey knit on all needles around the circumference of the welt; and
   (d) a fourth feed comprising an inlaid 1×1 rib at tuck height around the circumference of the welt.

7. The therapeutic medical garment according to claim 6, wherein the garment is a stocking, and the welt comprises between 40 and 50 knitting revolutions.

8. A therapeutic medical garment having a graduated pressure profile along its length, and comprising a knitted welt proximate one end thereof with a surface adapted for residing against the wearer's skin constructed of a ground yarn and a plurality of raised, skin-engaging stabilizer elements extending in spaced-apart relation around an inner surface of the welt to reduce a tendency of the welt to roll on itself, wherein the garment comprises a circular-knitted stocking for being worn on a leg, the stabilizer elements comprise a knitted structure extending substantially longitudinally along a length of the welt on an inner surface thereof, and include in a plurality of knitting revolutions forming the circular-knitted welt formed from:
   (a) a first feed comprising a jersey knit on all needles with a plurality of spaced-apart stabilizer bar yarns patterned into the welt around a circumference of the welt;
   (b) a second feed comprising a jersey knit on all needles with a plurality of spaced-apart float yarns patterned into the welt to provide additional bulk to the stabilizer elements;
   (c) a third feed comprising a jersey knit on all needles with a plurality of spaced-apart stabilizer bar yarns patterned into the welt around the circumference of the welt; and
   (d) a fourth feed comprising an inlaid 1×1 rib knitted at tuck height.

9. A therapeutic medical garment having a graduated pressure profile along its length, and comprising a knitted garment having:
   (a) a knitted welt proximate one end of the garment with an inwardly facing layer having a surface adapted for residing against a wearer's skin and including a ground yarn and a plurality of raised, skin-engaging stabilizer elements positioned on and extending in spaced-apart relation around an inwardly facing surface of the welt;
   (b) an outwardly facing layer; and
   (c) either the outwardly facing layer or the inwardly facing layer being configured so that in a use condition on a limb of a wearer a modulus of elasticity parallel to a longitudinal axis of the inwardly facing layer is greater than a modulus of elasticity parallel to the longitudinal axis of the outwardly facing layer, whereby a resistance of the selected outwardly or inwardly facing layer against a lengthening stress parallel to the longitudinal axis is increased such that if the welt begins to roll back on itself, the outwardly or inwardly facing layer will lengthen, and the resistance against a lengthening increases, the welt becomes more stable and is prevented from deflecting outwardly and rolling over itself.

10. The therapeutic medical garment according to claim 9, wherein the inwardly facing layer and the outwardly facing layer of the welt define a first annular connection at a top end of the garment, a second annular connection on the garment at a longitudinally spaced-apart location from the first annular connection, and a length of the inwardly facing layer and the outwardly facing layer between the first and second annular connections are separate from each other and define the longitudinal extent of the welt.

11. The therapeutic medical garment according to claim 9, wherein in a use condition on a limb of a wearer the stabilizer elements are prestressed such that they apply a force that tends to contract the inwardly facing layer parallel to the longitudinal axis but does not exert a force on the outwardly facing layer, thereby creating a tendency of the welt to deflect inwardly in opposition to a tendency of the welt to roll outwardly over itself.

12. The therapeutic medical garment according to claim 9, wherein the stabilizer elements are integrally formed with the inwardly facing layer of the welt.

13. The therapeutic medical garment according to claim 9, wherein the garment comprises a stocking.

* * * * *